United States Patent [19]

Koyama

[11] Patent Number: 4,615,983
[45] Date of Patent: Oct. 7, 1986

[54] IMMUNOLOGICAL MEASURING ELEMENT

[75] Inventor: Mikio Koyama, Hino, Japan

[73] Assignee: Konishiroku Photo Industry Co., Ltd., Tokyo, Japan

[21] Appl. No.: 319,391

[22] Filed: Nov. 9, 1981

[30] Foreign Application Priority Data

Nov. 11, 1980 [JP] Japan ................................ 55-157682

[51] Int. Cl.[4] ..................... G01N 33/54; G01N 33/58; G01N 1/48; B65D 71/00
[52] U.S. Cl. .................................... 436/514; 436/515; 436/530; 436/531; 436/535; 436/804; 436/807; 422/56; 422/57; 422/60; 422/69; 422/71
[58] Field of Search ..................... 424/1, 1.5; 422/56, 422/57, 60, 69, 71, 514, 515; 436/530, 531, 535, 804, 807

[56] References Cited

U.S. PATENT DOCUMENTS

| | | |
|---|---|---|
| 3,966,897 | 6/1976 | Renn et al. ................................ 424/1 |
| 4,094,647 | 6/1978 | Deutsch et al. ........................... 424/1 |
| 4,160,008 | 7/1979 | Fenocketti et al. ..................... 422/56 |
| 4,166,104 | 8/1979 | Wagner et al. ......................... 436/531 |
| 4,254,082 | 3/1981 | Schick et al. ............................. 424/1 |
| 4,292,272 | 9/1981 | Kitajima et al. ........................ 422/56 |
| 4,301,139 | 11/1981 | Feingers et al. ......................... 424/1 |
| 4,311,690 | 1/1982 | Buehler et al. ........................... 424/1 |
| 4,340,565 | 7/1982 | Kitajima et al. ........................ 422/56 |
| 4,356,149 | 10/1982 | Kitajima et al. ........................ 422/56 |
| 4,366,241 | 12/1982 | Tom et al. ................................ 424/1 |

Primary Examiner—Christine M. Nucker
Attorney, Agent, or Firm—Frishauf, Holtz, Goodman & Woodward

[57] ABSTRACT

There is presented a novel immunological element suitable for an immunological assay of an antigen according to the so called two antibody method, which element having two separate sheets, one being a sheet for reaction in which the reaction for formation of antigen-antibody bounds is carried out and the antigen-antibody bounds formed are immobilized, the other being a F receptor sheet in which unreacted free labelled antigen is transferred at a controlled rate to be received for analysis. This element enables separation between the bounds and the free labelled antigen by a simple operation without cumbersome separation procedures and is also excellent in storability.

35 Claims, 6 Drawing Figures

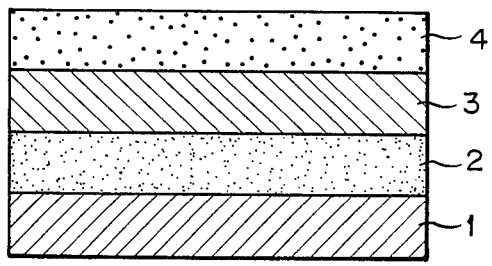
FIG. 1(a)
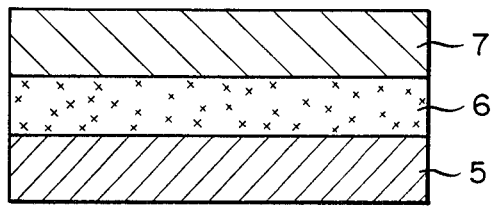
FIG. 1(b)
FIG. 2
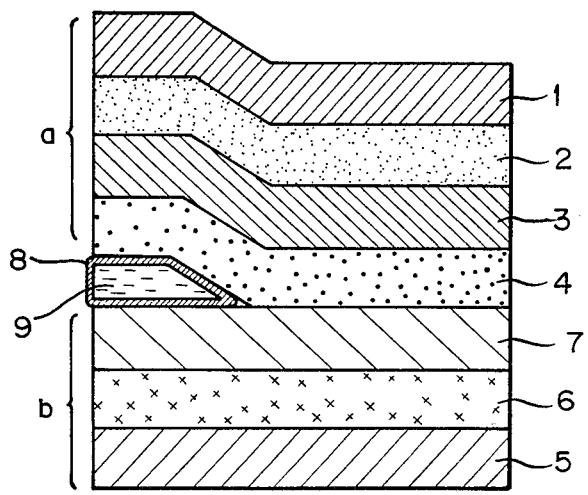

IMMUNOLOGICAL MEASURING ELEMENT

This invention relates to an immunological measuring element. More particularly, it pertains to an immunological measuring element which enables simple and precise operation for separation between antigen-antibody bound and free antigen according to the two antibody method and is also excellent in storability.

It is well known in the art to determine quantitatively an antigen (or an antibody) in a sample by allowing a fixed amount of a labelled antigen (or a labelled antibody), which is labelled with a radioisotope, an enzyme or a fluorescent tag, and an antigen (or an antibody) in a sample to be analyzed to react competitively with an antibody (or an antigen) and calculating from the ratio of the labelled antigen-antibody bound (Bound, hereinafter referred to as B) formed and the free labelled antigen (Free, hereinafter referred to as F) [B/F]. According to this measuring method, irrespective of which labelling agent is used, it is indispensably required to separate B formed from unreacted F. For example, in case of radioimmunoassay (RIA) wherein a radioisotope such as $^{125}I$ or $^{131}I$ is used as a tag, a scintillation counter is used to count the dosage of B and/or F for quantitative determination of both thereof, and hence it is necessary to separate B from F before said counting.

There have been proposed various methods for the separation B and F, but among them the two antibody method is the most popular for the advantage of relatively easier operation as compared with other methods, for example, being feasible in one test tube.

In the following, the description is made specifically with reference to the assay of an antigen in a sample.

According to the two antibody method, in addition to an antibody against an antigen to be assayed (a first antibody), there is employed a second antibody against said first antibody and B is permitted to be bound to the second antibody, thereby being converted to a precipitate, before separation from F. In the prior art, said two antibody method has been practiced by carrying out the second antigen-antibody reaction in a liquid in, for example, a test tube and separating the thus formed second antibody bound by centrifugation or filtration as a precipitate or a residue. However, according to this practice of prior art which is completely wet system, it is necessary to prepare a labelled antigen solution and antibody solution in addition to a sample for every operation. Further, cumbersome operations such as centrifugation or filtration are required to be performed for separation of B and F.

An object of the present invention is to provide an immunological measuring element which enables a highly precise measurement with easy separation of B and F, by overcoming the drawback of the prior art as described above with the use of a dry system measuring element in place of the completely wet system method of the prior art.

It is another object of the present invention to provide a dry system immunological measuring element excellent in storability, by use of which immunological measurement utilizing an antigen-antibody reaction is made possible only by a simple operation of the development of a sample.

According to the present invention, there is provided an immunological measuring element, comprising:

(a) a sheet for reaction having a liquid impervious support and a second antibody layer, provided on one side of said support, containing a hydrophilic colloid as matrix; and (b) a F receptor sheet having a liquid impervious support, a F receptor layer, provided on said support, consisting of a hydrophilic colloid, and a diffusion rate controlling layer provided on said F receptor layer.

According to a preferred embodiment of the present invention, there is also provided an immunological measuring element, comprising:

(a) a sheet for reaction having a liquid impervious support, a second antibody layer, provided on one side of said support, containing a protective colloid as matrix, a first antibody layer, provided on the upper side of said second antibody layer, containing a protective colloid as matrix and a diffusion rate controlling layer provided between said second antibody layer and said first antibody layer; and (b) a F receptor sheet having a liquid impervious support, a F receptor layer, provided on said support, consisting of a hydrophilic colloid, and a diffusion rate controlling layer provided on said F receptor layer.

The present invention may better be understood with reference to the accompanying drawings, in which:

FIG. 1(a) is a longitudinal sectional view of one embodiment of the immunological measuring element of this invention;

FIG. 1(b) is a longitudinal sectional view of one embodiment of the immunological measuring element of this invention;

FIG. 2 is a longitudinal sectional view of the element as shown in FIG. 1 which is assembled with a readily rapturable vessel interposed;

Figure 3:
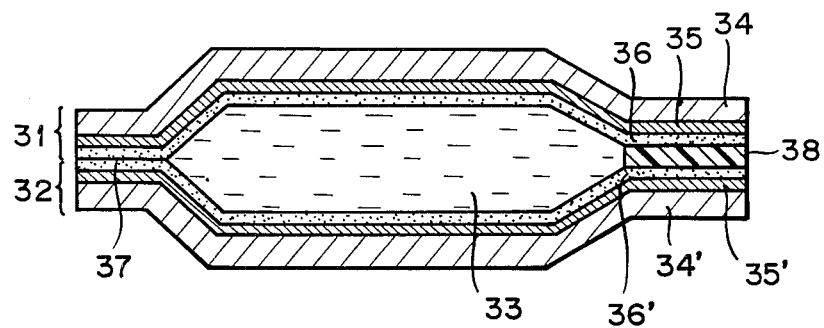
FIG. 3 is a longitudinal sectional view of a readily rapturable vessel containing a developer.

FIGS. 1(a), 1(b) and 2 show enlarged sectional views of the immunological measuring element of this invention, in which, however, the thicknesses for respective layers are markedly exaggerated for the purpose of illustration.

In FIG. 1(a) shows a sheet for reaction and FIG. 1(b) shows is a F receptor sheet.

The sheet for the reaction of FIG. 1(a) has a liquid impervious support 1, composed of, for example, polyethylene terephthalate, triacetyl cellulose, polystyrene, polycarbonate or other materials, and a second antibody layer 2 containing a second antibody superimposed on the support 1. The second antibody layer 2 contains a hydrophilic colloid as matrix so as to be sufficiently swellable with penetration of water through the layer. As the hydrophilic colloid, there may be mentioned gelatin, modified gelatin, polyvinyl alcohol, polyethylene glycol, polyvinyl pyrrolidone, polyalkylene oxide, and the like. The optimum swelling degree of the hydrophilic layer is 300 to 500%.

On the second antibody layer 2, there is further provided a first antibody layer 4 through an intermediary diffusion rate controlling layer 3.

The diffusion rate controlling layer 3 functions to control the diffusion rate of a sample solution or a developer. The diffusion rate can be controlled by varying the formulation ratio of the hydrophobic polymer and the hydrophilic polymer constituting said layer or the kinds of the polymers employed. The hydrophobic polymer may include, for example, cellulose acetate, acetyl pullulan, cellulose acetate butyrate, ethyl cellulose, polyvinyl acetate, a partial hydrolysate of polyvinyl acetate. On the other hand, the hydrophilic polymer may include (in addition to hydrolyzable polymers) polyacrylic acid, polymethacrylic acid, copolymers of acrylic acid, copolymers of methacrylic acid, polyphenylacrylate, copolymers of phenylacrylate, copolymers of maleic acid anhydride (e.g. maleic acid anhydride-styrene copolymer), etc. In general, these polymers are formulated so that the content of the hydrophilic polymer may be 2 to 50% by weight. The diffusion rate may also be controlled by selection of the degree of acetylation or molecular weight of the cellulose acetate employed or by the thickness of the layer. The diffusion rate controlling layer is generally preferred to have a dry film thickness of 0.2 to 20 $\mu$m.

The first antibody layer 4 is a layer constituted of a hydrophilic colloid as matrix similar to the second antibody layer and contains a first antibody. It may preferably have a thickness of about 5 to 50 $\mu$m.

Referring now to the constitution of the F receptor sheet shown in FIG. 1(b), there is provided, on a liquid impervious support 5 made from the same material as mentioned above such as polyethylene terephthalate, a F receptor layer 6, on which there is further provided a diffusion rate controlling layer 7. The F receptor layer 6 is a hydrophilic colloid layer, which receives F separated from B. The F receptor layer may preferably have a thickness of 10 to 50 $\mu$m.

The diffusion rate controlling layer 7 has the same constitution as the aforesaid diffusion rate controlling layer 3, and may have a thickness and the ratio of the hydrophobic polymer to the hydrophilic polymer, which are to be determined depending on the purpose. Its dry layer thickness is selected approximately within the range from 0.2 to 20 $\mu$m.

Next, the method for using the immunological element as described above is to be explained by assaying the quantity of an antigen in a sample according to the radioimmunoassay method.

First, a solution containing the sample to be assayed and the labelled antigen in predetermined quantities, respectively, is incubated by developing on the sheet for reaction shown in FIG. 1(a). Said incubation may preferably be carried out at 2° to 25° C. for 0.5 to 36 hours. The sample solution added to the first antibody layer 4 of the sheet for reaction gradually diffuses downward while its diffusion rate is suppressed by the diffusion rate controlling layer 3. During this procedure, in the first antibody layer, the antigen in the sample and the labelled antigen react competitively with the first antibody to form labelled antigen-antibody and free antigen-antibody complexes. With lapse of time, the antigen-antibody and free antigen further penetrate downward until they reach the second antibody layer 2, whereupon there occurs the second antigen-antibody reaction. As the result, the bound antigen-antibody finds to the second antibody to form the antigen-antibody-second antibody complex. The antigen-antibody-second antibody complex has a very large molecular weight on the order of several thousands to some hundred thousands and hence is immobilized on the second antibody layer until it can no longer be displaced even by the later application of a developer. Thus, B is deposited as labelled antigen-antibody-second antibody complex in the second antibody layer to be immobilized therein.

As the next step, the sheet for the reaction with its topside facing downward is superimposed on the F receptor sheet, and a developer is added between the sheets to carry out development. The function of the developer is to transfer free labelled antigens (F) remaining unreacted in the sheet for the reaction to the sheet for F receptor. After addition of the developer, the sheet is left to stand for about 0.5 to 12 hours, which standing time may freely be selected so long as it is longer than a certain minimum length of time. The separation efficiency between F and B can be improved as the standing time is increased.

As the developer to be used, even water may be available in some cases, but it is usually desirable to use a buffer (e.g. a phosphate buffer) of pH 7 to 6, a carrier protein (e.g. bovine serum albumin, goat serum albumin, house rabbit serum albumin) and isotonic sodium chloride solution, a viscous liquid (e.g. hydroxyethyl cellulose, sodium carboxymethyl cellulose, natural gum) in combination in a desirable formulation.

As shown in FIG. 2, for development of the developer between the sheet a for the reaction and the sheet b for F receptor, it is convenient to interpose a readily rupturable vessel 8 containing a developer 9 between the two sheets and then permit the thus prepared assembly to pass through a pair of rollers. According to this method, the readily rupturable vessel is broken when passsing through the rollers to release the developer, which is in turn spread in a uniform layer between the two sheets. As the readily rupturable vessel to be used herein, there may be mentioned those as disclosed in U.S. Pat. Nos. 2,543,181, 2,643,886, 2,653,782 and 2,723,051. One example of a preferred embodiment is shown in FIG. 3 (crosssectional view).

The rupturable vessel is constituted of two rectangular sheets 31 and 32, one being superimposed on and adhered to the other at the four sides thereof, contains a developer 33 sealed therein. Each of the sheets 31 and 32 has a laminated structure, having a support layer 34 (e.g. paper, flexible polymer), a metal foil 35 (e.g. lead, aluminum, tin, etc.) and a thermoplastic polymer 36 (e.g. polyethylene, modified polyethylene, polyvinyl chloride) successively laminated. The sheets 31 and 32 were superimposed one on the other so that the surfaces of the thermoplastic polymer may face each other, and they are hot-melted to each other at the three sides thereof. In FIG. 3, the portion 37 is the hot-melted portion at which the thermoplastic polymers 36 are bonded to each other, which portion has a considerably strong peel strength. At the residual one side, heating is effected with another thermoplastic polymer 38 interposed between the thermoplastic polymers 36 and 36' for fusion bonding of these polymers. As the thermoplastic polymer 38, for example, a mixture of polyvinyl chloride-polyvinyl acetate or polyvinylidene chloride-ethyl cellulose is useful and can give a fusion bonding with weaker strength, as compared with those at other three sides. For this reason, under a pressure applied, only the bonding at the weakly bonded one side will be ruptured to release the developer contained therein to the outside of the vessel.

After development of the developer, the sheet for the reaction is separated from the F receptor sheet, and the radioactivity of the sheet for the reaction and/or the F receptor sheet is measured by a scintillation counter to determine B/F, from which the quantity of an antigen in the sample is determined with reference to the calibration curve previously prepared.

In the element according to the present invention, F cannot completely be transferred to the F receptor layer, even if development may be carried out for a sufficiently long time. This, however, is no problem as to the function of the element, since the constitution of the element, the composition of each layer, its thickness, the composition and quantity of the developer, the development time and other parameters are standardized, and the calibration curve is prepared based on such standards and used for measurement.

In the embodiment as described above, the diffusion rate of the developer is controlled by the diffusion rate controlling layers 3 and 7. It is also possible to accelerate the diffusion rate by interposing a water absorptive layer between, for example, the support 5 and the F receptor 6 or between the support 1 and the second antibody layer 2. As the material for such a water absorptive layer, there may be used swellable polymers known in the art, including polyethylene oxide, polyethylene glycol, polyvinyl alcohol, polyvinyl pyrrolidone, hydrolysate of acrylonitrile-grafted starch, gelatin and modified gelatin.

Figure 4A:
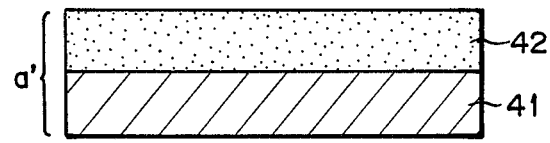
FIG. 4(a) is a longitudinal sectional view of another embodiment of the immunological measuring element of this invention.
Figure 4B:
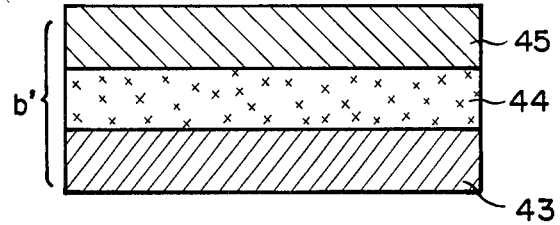
FIG. 4(b) is a longitudinal sectional view of another embodiment of the immunological measuring element of this invention.

The immunological measuring element as described above is capable of performing all of the first antigen-antibody reaction, the second antigen-antibody reaction and separation between B and F. By omitting a part of such an element, it is also possible to provide an element for separation between B and F. FIG. 4 shows an embodiment of such an immunological measuring element, in which FIG. 4(a) shows a sheet a' for the reaction for carrying out only the second antigen-antibody reaction. On the liquid impervious support 41, there is laminated the second antibody layer 42 containing the second antibody. FIG. 4(b) shows an F receptor sheet b', having the same constitution as the F receptor sheet as in the element shown in FIG. 1, in which the F receptor layer 44 is provided on the liquid impervious support 43 and further the diffusion rate controlling layer 45 is provided thereon. This element corresponds exactly to the element as shown in FIG. 1 from which the diffusion rate controlling layer 3 and the first antibody layer 4 are removed. The residual common layers are each constituted similarly. This immunological measuring element is to be used for the separation of B and F. That is, a solution, in which the first antigen-antibody reaction has been completed in, for example, a test tube, is added onto the sheet for the reaction of this element to carry out incubation. The second antigen-antibody reaction thereby occurs and B is deposited as the labelled antigen-antibody-second antibody bound on the second antibody layer to be immobilized therein. As the next step, the sheet for the reaction as shown in FIG. 4(a) is turned upside down to be superimposed on the F receptor sheet as shown in FIG. 4(b) so that the second antibody layer 42 may be contacted with the diffusion rate controlling layer 45, followed by development with a developer between both sheets using, for example, a readily rupturable developer container. With lapse of time, F is transferred to the F receptor 44, thereby to effect separation of B and F.

Then, the sheet for the reaction is separated from the F receptor sheet. In case of radioimmunoassay, radioactivity in each sheet can be counted to determine B/F, from which the quantity of the antigen can be determined with reference to the calibration curve previously prepared.

As apparently seen from the above description, by use of the immunological measuring element according to the present invention, separation of B and F can be carried out without cumbersome operations such as centrifugation or filtration, and the measurement can be performed with high precision as well as good reproducibility. The element of the present invention is excellent in storability, and the measurement can be proceeded by a simple operation.

With respect to developing a liquid containing a sample, it has also another advantage of being capable of subjecting a large number of test samples efficiently to measurement.

Although, the immunological measuring element of the present invention has been described primarily with reference to application to radioimmunoassay, it can also be used when using other substances such as enzymes or fluorescent substances as a target. In case of enzymeimmunoassay using an enzyme, a substrate reacting specifically with the enzyme employed may be previously contained in the receptor layer or the receptor layer may be immersed in the solution containing the substrate to thereby permit the enzyme to react with the substrate, said reaction being detected and measured by a suitable means. When using a fluorescent substance as a target, light may be irradiated on the F receptor layer after separation, and the intensity of fluorescence generated may be measured.

EXAMPLE 1

(A) Sheet for reaction

A sheet for reaction was prepared by coating successively the aqueous solutions containing the components of the respective layers shown below on a support of a transparent polyethylene terephthalate with a thickness of 150 μm, followed by drying.

(1) The second antibody layer

Composition

| | |
|---|---|
| Anti-rabbit γ-globulin goat serum (produced by Dinabot RIA Research) | 1 ml/100 cm² |
| Deionized gelatin | 25 mg/100 cm² |

Thickness of dry film: about 2.5 μm.

(2) The diffusion rate controlling layer

Composition

| | |
|---|---|
| Cellulose acetate (degree of acetylation 40%) | 7 mg/100 cm² |
| Styrene-maleic acid anhydride copolymer | 3 mg/100 cm² |

Thickness of dry film: about 1 μm.

(3) The first antibody layer

Composition

| | |
|---|---|
| Anti-α-fetoprotein rabbit serum (produced by conventional method) | 1 ml/100 cm² |
| Nomal rabbit serum | 1 ml/100 cm² |

-continued

| | |
|---|---|
| Deionized gelatin | 120 mg/100 cm² |

Thickness of dry film: about 12 μm.

(B) F receptor layer

Then, on a support of a transparent polyethylene terephthalate with a thickness of 150 μm, the aqueous solutions of the components of the respective layers shown below were successively coated and dried to prepare a F receptor sheet.

(1) F receptor layer

Composition

| | |
|---|---|
| Deionized gelatin | 200 mg/100 cm² |

Thickness of dry film: about 20 μm.

(2) The diffusion rate controlling layer

Composition

| | |
|---|---|
| Cellulose acetate (degree of acetylation 40%) | 6 mg/100 cm² |
| Maleic acid anhydride-styrene copolymer | 4 mg/100 cm² |

Thickness of dry film: about 1 μm.

(3) Readily rapturable vessel

A developer having the following composition was prepared and 3 ml of this developer was sealed in a readily rapturable vessel having the structure as shown in FIG. 3.

Composition of developer

| | |
|---|---|
| Horse serum albumin | 0.003 g |
| Hydroxyethyl cellulose | 0.001 g |
| Phosphate buffer-isotonic sodium chloride solution | 0.3 ml |

Then, five kinds of standard serum having concentrations of α-fetoprotein of 100, 200, 300, 400 and 500 ng/ml were prepared and to each 0.1 ml of the standard serum were added 0.5 ml of a diluting solution and 0.1 ml of $^{131}$I-labelled α-fetoprotein. Each mixture thus prepared was developed on the sheet for reaction as prepared above. The diluting solution employed was a phosphate buffer-isotonic sodium chloride solution containing 1% horse serum albumin, and the $^{131}$I-labelled α-fetoprotein was labelled according to the chloramine T method and has a specific radioactivity of 10,000 cpm.

After development of the aforesaid solution on the sheet for reaction, incubation was carried out at 4° C. for 40 hours, and thereafter the sheet for reaction was superposed on the F receptor sheet with the side of the support upward. The readily rapturable vessel was thereby placed so as to be interposed between the two sheets, followed by breaking of the vessel to permit the developer to develop between the two sheets. Thus, the whole assembly was left to stand at room temperature for one hour.

Then, the two sheets were separated from each other and the radioactivity of the sheet for reaction was measured by a scintillation counter. The results are shown in Table 1.

TABLE 1

| α-fetoprotein concentration in standard serum (ng/ml) | Radioactivity ($\times 10^3$ cpm) |
|---|---|
| 100 | 2.511 |
| 200 | 1.902 |
| 300 | 1.633 |
| 400 | 1.508 |
| 500 | 1.364 |

EXAMPLE 2

(A) Sheet for reaction

A sheet for reaction was prepared by coating an aqueous solution containing the following components on a support of a transparent polyethylene terephthalate with a thickness of 100 μm.

| | |
|---|---|
| Anti-rabbit γ-globulin goat serum (produced by Dinabot RIA Research) | 1 ml/100 cm² |
| Gelatin | 20 mg/100 cm² |

(B) F receptor sheet

On a transparent polyethylene terephthalate support with a thickness of 100 μm, there were successively coated the aqueous solutions containing the components for the respective layers shown below, followed by drying, to prepare a F receptor sheet.

(1) F receptor layer

Composition

| | |
|---|---|
| Gelatin | 200 mg/100 cm² |

Thickness of dry film: about 20 μm.

(2) Diffusion rate controlling layer

Composition

| | |
|---|---|
| Cellulose acetate (Degree of acetylation 40%) | 20 mg/100 cm² |
| Polyacrylic acid | 2 mg/100 cm² |

(C) Developer

In the same readily rapturable vessel as used in Example 1, 0.3 ml of a developer having the following composition was sealed.

COMPOSITION OF DEVELOPER

| | |
|---|---|
| Horse serum albumin | 0.003 g |
| Hydroxyethyl cellulose | 0.001 g |
| Phosphate buffer-isotonic sodium chloride solution | 0.3 ml |

Then, five kinds of standard serum with α-fetoprotein concentrations of 100, 200, 300, 400 and 500 ng/ml respectively, were prepared and to each 0.1 ml of the standard serum was added the following ①  to ④, followed by incubation at 4° C. for 24 hours.

| | | |
|---|---|---|
| ① | Diluting solution (phosphate buffer-isotonic sodium chloride solution containing 1% horse serum albumin) | 0.5 ml |
| ② | $^{131}$I-labelled α-fetoprotein (10,000 cpm) (labelled according to the chloramine T method) | 0.1 ml |
| ③ | Anti-α-fetoprotein rabbit serum | 0.1 ml |
| ④ | Normal rabbit serum | 0.1 ml |

Each sample after incubation was developed on the sheet for reaction as prepared above, and incubation was conducted at 4° C. for 24 hours.

Subsequently, both sheets were superposed so that the second antibody layer of the sheet for reaction may be contacted with the diffusion rate controlling layer of the F receptor layer. The readily rapturable vessel was interposed between the two sheets and the developer was released by breaking of the vessel to carry out development between the sheets at room temperature for one hour. Then, the two sheets were separated from each other and the radioactivity of the sheet for reaction was measured by a scintillation counter. The results are shown in Table 2 together with Comparative example.

Comparative example (centrifugal precipitation method)

Similarly as in Example 2, five kinds of standard serum with α-fetoprotein concentrations of 100, 200, 300, 400 and 500 ng/ml were prepared, and to each 0.1 ml of the standard serum was added each of ① to ④ in the same quantity as in Example 2, followed by incubation at 4° C. for 24 hours.

Then, 0.1 ml of anti-rabbit γ-globulin goat serum (produced by Dinabot RIA Research) was added to each of the above mixtures to carry out incubation similarly. After incubation, the precipitate was separated by centrifugation at 3,000 rpm for 30 minutes and its radioactivity was measured by a well-type scintillation counter. The results are shown also in Table 2.

TABLE 2

| α-fetoprotein concentration in standard serum (ng/ml) | Example 2 ($\times 10^3$ cpm) | Comparative example ($\times 10^3$ cpm) |
|---|---|---|
| 100 | 2.409 | 2.316 |
| 200 | 1.869 | 1.789 |
| 300 | 1.621 | 1.526 |
| 400 | 1.449 | 1.342 |
| 500 | 1.340 | 1.211 |

EXAMPLE 3

Using the immunological measuring element as used in Example 1, the same procedure as in Example 1 was repeated 50 times for measurement of the artificial serum with α-fetoprotein concentrations of 100 ng/ml, 300 ng/ml and 500 ng/ml and human serum containing α-fetoprotein to examine the coefficient of variation (C.V.) of measurement values.

At the same time, using artificial serum and human serum, measurement was also repeated for 50 times by the centrifugal precipitation method with the use of a solution system of prior art for comparison with respect to C.V. The results are also shown in Table 3.

TABLE 3

| Test sample | Element of this invention (C.V.) | Prior art |
|---|---|---|
| 100 ng/ml | 1.33% | 2.33% |
| 300 ng/ml | 1.56% | 3.86% |
| 500 ng/ml | 1.45% | 4.92% |
| Human serum | 1.76% | 5.32% |

As apparently seen from Table 3, the immunological measuring instrument of the present invention shows better reproducibility than the method of prior art.

What we claim is:

1. In an immunoassay method for the qualitative and quantitative determination of an antigen in a sample and further including a labelled form of said antigen; a first antibody which is capable of binding to said antigen and said labelled antigen; and a second antibody which is capable of binding to said first antibody; wherein said antigen and said labelled antigen undergo a competitive binding reaction with said first antibody to produce first antibody bound complexes of said antigen and said labelled antigen, and separating said first antibody bound complexes from unreacted labelled antigen, the improvement comprising:

(a) contacting said first antibody complexes with a reaction zone of an immunological element, said reaction zone comprising a liquid impervious support and a layer provided on one side of said support, said layer containing said second antibody and contaning a matrix of a hydrophilic colloid, wherein said first antibody complexes react with said second antibody to form immobilized complexes thereof in said second antibody containing layer;

(b) superimposing said reaction zone on a receiving zone of said immunological element, said receiving zone for receiving said unreacted labelled antigen and comprising a liquid impervious support; a receiving layer for receiving said labelled antigen, said receiving layer provided on said support and containing a matrix of a hydrophilic colloid; and a diffusion rate controlling layer consisting essentially of a combination of hydrophilic polymer and a hydrophobic polymer, said diffusion rate controlling layer being provided on said receiving layer, said reaction zone being superimposed in a manner in which said liquid impervious supports are at opposed ends of said superimposed zones and said second antibody layer of said reaction zone is in contact with said diffusion rate controlling layer of said receiving zone, whereby said unreacted labelled antigen migrates from said reaction zone into the receiving layer of said receiving zone via said diffusion rate controlling layer;

(c) measuring the amount of the unreacted labelled antigen in said receiving layer or the amount of the immobilized complex containing said labelled antigen in said second antibody containing layer; and (d) determining the amount of said antigen in said sample by comparing the amount of the unreacted labelled antigen or the amount of the immobilized complex containing said labelled antigen to a standared solution containing a known amount of said antigen.

2. The method of claim 1, further comprising introducing a developer between said superimposed reaction zone and receiving zone whereby said developer mixes with said migrating unreacted labelled antigen and said mixture migrates to said receiving layer of said receiving zone.

3. The method of claim 2, wherein said developer is in the form of a solution contained within a rupturable vessel and thereafter released upon rupture of said rupturable vessel.

4. In an immunoassay method of the qualitative and quantitative determination of an antigen in a sample and further including a labelled form of said antigen; a first antibody which is capable of binding to said antigen and said labelled antigen; and a second antibody which is capable of binding to said first antibody, the improvement comprising:

(a) contacting said sample with a reaction zone of an immunological element, said reaction zone comprising a liquid impervious support, a layer provided on one side of said support, said layer containing said second antibody and containing a matrix of a hydrophilic colloid, a diffusion rate controlling layer consisting essentially of a combination of a hydrophilic polymer and a hydrophobic polymer on said second antibody containing layer and a layer containing said first antibody on said diffusion rate controlling layer, wherein said antigen and said labelled antigen undergo a competitive binding reaction with said first antibody to produce first antibody complexes of said antigen and said labelled antigen, and wherein said first antibody complexes react with said second antibody in said second antibody layer to form immobilized complexes of said antigen and immobilized complexes of said labelled antigen;

(b) superimposing said reaction zone on a receiving zone of said immunological element, said receiving zone for receiving said unreacted labelled antigen and comprising a liquid impervious support; a receiving layer for receiving said labelled antigen, said receiving layer provided on said support and containing a matrix of a hydrophilic colloid; and a diffusion rate controlling layer consisting essentially of a combination of a hydrophilic polymer and a hydrophobic polymer, said diffusion rate controlling layer being provided on said receiving layer, said reaction zone being superimposed in a manner in which said liquid impervious supports are at opposed ends of said superimposed zones and said second antibody layer of said reaction zone is in contact with said diffusion rate controlling layer of said receiving zone, whereby said unreacted labelled antigen migrates from said reaction zone into the receiving layer of said receiving zone via said diffusion rate controlling layer;

(c) measuring the amount of the unreacted labelled antigen in said receiving layer or the amount of the immobilized complex containing said labelled antigen in said second antibody containing layer; and (d) determining the amount of said antigen in said sample by comparing the amount of the unreacted labelled antigen or the amount of the immobilized complex containing said labelled antigen to a standard solution containing a known amount of said antigen.

5. The method of claim 4, further comprising introducing a developer between said superimposed reaction zone and receiving zone whereby said developer mixes with said migrating unreacted labelled antigen and said mixture migrates to said receiving layer of said receiving zone.

6. The method of claim 5, wherein said developer is in the form of a solution contained within a rupturable vessel and thereafter released upon rupture of said rupturable vessel.

7. The method of claim 4, wherein the hydrophilic colloid of at least one of said reaction zone and said receiving zone is selected from the group consisting of gelatin, modified gelatin, polyvinyl alcohol, polyethylene glycol, polyvinyl pyrrolidone and polyethylene oxide.

8. The method of claim 7, wherein said developer is contained with a rupturable vessel interposed between said superimposed reaction zone and receiving zone.

9. The method of claim 4, wherein said labelled antigen consists essentially of an antigen labelled with a member selected from the group consisting of a radioisotope, a fluorescer, an enzyme, and an enzyme substrate.

10. The method of claim 4, wherein the step of measuring the unreacted labelled antigen or the amount of immobilized complex containing the labelled antigen further comprises separating said superimposed reaction zone from said receiving zone.

11. The method of claim 1, wherein the step of measuring the amount of unreacted labelled antigen or immobilized complex containing said labelled antigen further comprises separating said superimposed reaction and receiving zones.

12. The method of claim 4, wherein the step of measuring the amount of unreacted labelled antigen or immobilized complex containing said labelled antigen further comprises separating said superimposed reaction and receiving zones.

13. The method of claim 1, wherein the hydrophilic colloid of at least one of said reaction zone and said receiving zone is selected from the group consisting of gelatin, modified gelatin, polyvinyl alcohol, polyethylene glycol, polyvinyl pyrrolidone and polyethylene oxide.

14. The method of claim 13, wherein the step of passing said unreacted labelled antigen further comprises:

(a) superimposing said reaction zone on said receiving zone in a manner in which said liquid impervious supports are at opposed ends of said superimposed zones;

(b) introducing a developer solution between said superimposed reaction zone and receiving zone whereby said developer solution containing said unreacted labelled antigen migrates to said receiving layer.

15. The method of claim 1, wherein said developer is contained with a rupturable vessel interposed between said superimposed reaction zone and receiving zone.

16. The method of claim 1, wherein said labelled antigen consists essentially of an antigen labelled with a member selected from the group consisting of a radioisotope, a fluorescer, an enzyme and an enzyme substrate.

17. The method of claim 1, wherein said labelled antigen consists essentially of an antigen labelled with a member selected from the group consisting of a radioisotope, a fluorescer, an enzyme, and an enzyme substrate.

18. The method of claim 1, wherein the step of measuring the unreacted labelled antigen or the amount of immobilized complex containing the labelled antigen further comprises separating said superimposed reaction zone from said receiving zone.

19. An immunological measuring element for use in an immunoassay method wherein the components of said method include a fluid sample suspected of containing one member of a binding pair selected fron antigen and a first antibody; a labelled form of said one member of said binding pair; and the other member of said binding pair; said immunological measuring element comprising in combination
(a) a reaction zone for receiving said fluid sample, said reaction zone comprising a liquid impervious support and a layer provided on one side of said support, said layer containing a second antibody capable of binding to said first antibody and containing a matrix of a hydrophilic colloid;
(b) a receiving zone for receiving said labelled form of said one member of said binding pair, said receiving zone comprising a liquid impervious support; a receiving layer for receiving said labelled form of said one member of said binding pair, said receiving layer provided on said support and containing a matrix of s hydrophilic colloid; and a diffusion rate controlling layer consisting essentially of a combination of a hydrophilic polymer and a hydrophobic polymer, said diffusion rate controlling layer being provided on said receiving layer;
wherein said reaction zone and said receiving zone are mutually adapted so that said reaction zone can be superimposed on said receiving zone so that said first antibody layer of said reaction zone is in contact with the diffusion rate controlling layer of said receiving zone; and
(c) comprising a rupturable vessel interposed between said second antibody layer and superimposed diffusion rate controlling layer of said reaction zone and said receiving zone; respectively, said rupturable vessel containing a developer.

20. The immunological measuring element of claim 19, wherein the hydrophilic colloid of at least one of said reaction zone and said receiving zone is selected from the group consisting of gelatin, modified gelatin, polyvinyl alcohol, polyethylene glycol, polyvinyl pyrrolidone and polyethylene oxide.

21. The immunological measuring element of claim 20, wherein the hydrophilic colloid has a swelling degree of 300 to 500%.

22. The immunological measuring element of claim 19, wherein the diffusion rate controlling layer contains 2 to 50% of said hydrophilic polymer.

23. The immunological measuring element of claim 22, wherein the hydrophilic polymer is at least one polymer selected from the group consisting of hydrolyzable polymers, polyacrylic acid, polymethacrylic acid, copolymers of acrylic acid, copolymers of methacrylic acid, polyphenylacrylate, copolymers of phenylacrylate and copolymers of maleic acid anhydride, and the hydrophobic polymer is at least one polymer selected from the group consisting of cellulose acetate, acetyl pullulan, cellulose acetate butyrate, ethyl cellulose, polyvinyl acetate, and a partiaal hydrolysate of polyvinyl acetate.

24. The immunological measuring element of claim 19, wherein the diffusion rate controlling layer has a thickness of 0.2 to 20 μm.

25. The immunological measuring element of claim 19, wherein the receiving layer has a thickness of 10 to 50 μm.

26. An immunological measuring element for use in an immunoassay method wherein the components of said method include a fluid sample suspected of containing an antigen and a labelled form of said antigen, said immunological measuring element comprising:
(a) a reaction zone for receiving said fluid sample, comprising a liquid impervious support; a layer containing a second antibody which is capable of binding to a first antibody, said layer provided on one side of said support and containing a matrix of a protective colloid; a layer containing said first antibody, said first antibody being capable of binding to said antigen, said first antibody layer provided on the upperside of said second antibody layer and containing a matrix of a protective colloid; and a diffusion rate controlling layer provided between said second antibody layer and said first antibody layer;
(b) a receiving zone for receiving said labelled antigen, said receiving zone comprising a liquid impervious support; a receiving layer for receiving said labelled antigen, said receiving layer provided on said support and containing a hydrophilic colloid; and a diffusion rate controlling layer consisting essentially of a combination of a hydrophilic polymer and a hydrophobic polymer, said diffusion rate controlling layer being provided on said receiving layer;
wherein said reaction zone and said receiving zone are mutually adapted so that said reaction zone can b superimposed on said receiving zone so that said first antibody layer of said reaction zone is in contact with the diffusion rate controlling layer of said receiving zone; and
(c) comprising a rupturable vessel interposed between said second antibody layer and superimposed diffusion rate controlling layer of said reaction zone and said receiving zone; respectively, said rupturable vessel containing a developer.

27. The immunological measuring element of claim 26, wherein the liquid impervious support of at least one of said reaction zone and said receiving zone consists essentially of a material selected from the group consisting of polyethylene terephthalate, triacetyl cellulose, polystyrene and polycarbonate.

28. The immunological measuring element of claim 27, wherein the hydrophilic colloid of at least one of said reaction zone and said receiving zone is selected from the group consisting of gelatin, modified gelatin, polyvinyl alcohol, polyethylene glycol, polyvinyl pyrrolidone and polyethylene oxide.

29. The immunological measuring element of claim 28, wherein the hydrophilic colloid has a swelling degree of 300 to 500%.

30. The immunological measuring element of claim 27, wherein the diffusion rate controlling layer contains 2 to 50% of said hydrophilic polymer.

31. The immunological measuring element of claim 30, wherein the hydrophilic polymer is at least one polymer selected from the group consisting of hydrolyzable polymers, polyacrylic acid, polymethacrylic acid, copolymers of acrylic acid, copolymers of methacrylic acid, polyphenylacrylate, copolymers of phenylacrylate and copolymers of maleic acid anhydride, and the hydrophobic polymer is at least one polymer selected from the group consisting of cellulose acetate, acetyl pullulan, cellulose acetate butyrate, ethyl cellulose, polyvinyl acetate, and a partial hydrolysate of polyvinyl acetate.

32. The immunological measuring element of claim 27, wherein the diffusion rate controlling layer has a thickness of 0.2 to 20 μm.

33. The immunological measuring element of claim 27, wherein the receiving layer has a thickness of 10 to 50 μm.

34. The immunological measuring element of claim 27, wherein the liquid impervious support of at least one of said reaction zone and said receiving zone is a material selected from the group consisting of polyethylene terephthalate, triacetyl cellulose, polystyrene and polycarbonate.

35. The immunological measuring element of claim 27, wherein the first antibody layer has a thickness of about 5 to 20 μm.

* * * * *